US006514539B1

(12) United States Patent
Courtney

(10) Patent No.: US 6,514,539 B1
(45) Date of Patent: Feb. 4, 2003

(54) **ANTIMICROBIAL COMPOSITION COMPRISING *LEPTOSPERMUM SCOPARIUM* AND *MELALEUCA ALTERNIFOLIA* OILS**

(75) Inventor: William John Courtney, Auckland (NZ)

(73) Assignee: Coast Biologicals Limited, Auckland (NZ)

( * ) Notice: Subject to any disclaimer, the term of this patent is extended or adjusted under 35 U.S.C. 154(b) by 0 days.

(21) Appl. No.: 09/831,053

(22) PCT Filed: Nov. 5, 1999

(86) PCT No.: PCT/NZ99/00194

§ 371 (c)(1),
(2), (4) Date: May 4, 2001

(87) PCT Pub. No.: WO00/27206

PCT Pub. Date: May 18, 2000

(30) Foreign Application Priority Data

Nov. 6, 1998 (NZ) ................................................ 332694

(51) Int. Cl.[7] .......................... A61K 35/78; A01N 25/34
(52) U.S. Cl. ........................................ 424/725; 424/404
(58) Field of Search ................................. 424/725, 404

(56) References Cited

U.S. PATENT DOCUMENTS 5,906,825 A * 5/1999 Seabrook et al. ........... 424/404

FOREIGN PATENT DOCUMENTS

| DE | 29719141 | * | 12/1997 |
| DE | 19631037 | * | 2/1998 |
| DE | 19631 037 A1 | | 2/1998 |
| WO | WO 98/42386 | | 10/1998 |

OTHER PUBLICATIONS

Kent, A.J. Australian Tea Trees of Economic Value, Sydney, Australia, I.S.O., Government Printer, 1929 (pp. 3–13).
Penfold, A.R. et al. "Tea Tree" Oils, Essential Oils of the Plant Family *Myrtaceae*, Museum of Technology and Applied Science, Sydney, Australia, 526–546 (1950).
Penfold, A.R. et al. The Germicidal Values of Some Australian Essential Oils and Their Pure Constituents, Read before the Royal Society of New South Wales, 346–350 (1925).
Raman, A. et al. Antimicrobial effects of tea–tree oil and its major components on *Staphylococcus aureus, Staph. epidermidis* and *Propoinibacterium acnes*, Letters in Applied Microbiology, 21:242–245 (1995).
Carson, C.F. et al. Antimicrobial activity of the major components of the essential oil of *Melaleuca alternifolia*, Journal of Applied Bacteriology, 78:264–269 (1995).

* cited by examiner

Primary Examiner—Christopher R. Tate
Assistant Examiner—Kailash C. Srivastava
(74) Attorney, Agent, or Firm—Brown Martin Haller & McClain LLP

(57) ABSTRACT

This invention relates to improvements in and relating to antimicrobial compositions. More particularly, it relates to antimicrobial compositions comprising or including a mixture of oils of *melaleuca alternifolia* and *leptospermum scoparium* and/or fractions or dilutions of same. A method of producing the composition is also claimed, as are methods of producing compositions which target particular microbes.

23 Claims, No Drawings

ANTIMICROBIAL COMPOSITION COMPRISING *LEPTOSPERMUM SCOPARIUM* AND *MELALEUCA ALTERNIFOLIA* OILS

TECHNICAL FIELD

This invention relates to improvements in and relating to antimicrobial compositions. More particularly, it relates to antimicrobial compositions comprising or including a mixture of oils of *melaleuca alternifolia* and *leptospermum scoparium* and/or fractions/dilutions of same.

BACKGROUND ART

In recent years increased effort has been devoted to investigating and isolating commercially useful extracts from native plants and animals internationally. In some respects this has been motivated by continuing resistance developed by infective organisms and diseases to conventional therapies but also by a desire to extract full benefit from the world's resources. In some cases the biological organism can be chemically active in its raw state, but more usually isolation or other treatment is necessitated to release the therapeutic and/or prophylactic effects. In New Zealand, essential oils have been extracted from New Zealand manuka tree (*leptospermum scoparium*) on a commercial basis for some years although the industry continues to grow. Manuka oil has been used to date in various applications including aromatherapy, cosmetics[1] and as a toothpaste ingredient. According to one source[2] manuka is the most abundant and widely distributed flowering native tree in New Zealand. It was historically used in New Zealand by Maori and later European settlers for purposes including the treatment of respiratory ailments, burns, dandruff, dysentery, fever, and indigestion, as well as being drunk as a type of tea. The biologically active ingredient is the oil accumulated in oil glands in the leaves. Whilst research[3] indicates that there may be different chemotypes of manuka in New Zealand, the present invention relates to all New Zealand chemotypes, although particular reference is made to manuka derived from the East Cape region of New Zealand.

[1]Kennedy & Myleck (1998) *A Downunder Perspective on Botanicals in Cosmetics*, Botanicals in Cosmetics, Marcel Dekker Inc., Impress (1998)
[2]Perry et al, *Essential Oils from New Zealand Manuka and Kanuka: Chemotexonomy of Leptospermum*, Phytochemistry 44(8): 1485 to 1495 (1997)
[3]Perry et al 1997 as above Manuka, whilst colloquially known in New Zealand as "the tea tree" is a completely different species to the Australian tea tree (*melaleuca alternifolia*).

Given the prevalence of the manuka and Australian tea trees in their respective countries, together with a wish to further investigate the biological properties of these species, it would be desirable to identify and apply the biological properties in a commercially and biologically useful manner.

It is an object of the present invention to address the foregoing problems or at least to provide the public with a useful choice.

Further aspects and advantages of the present invention will become apparent from the ensuing description, which is given by way of example only.

DISCLOSURE OF INVENTION

According to one aspect of the present invention there is provided a method of preparing a broad spectrum antimicrobial composition comprising combining the oils of *leptospermum scoparium* and *melaleuca alternifolia*.

Use of the combination is clearly highly advantageous over use of the whole oils individually.

In addition to whole oils, active (that is, having microbial activity or activity against microbes) antimicrobial dilutions and/or fractions of same are within the scope of the present invention.

Conventional oil extraction methods are well known, and may be used to extract the oils, or fractions of same, from the two trees or species.

According to another aspect of the present invention there is provided a method of preparing an antimicrobial composition, substantially as described above, to have effect against a targeted microbe comprising altering the proportions of the constituent *leptospermum scoparium* or *melaleuca alternifolia* oils as appropriate to specifically target said targeted microbe.

The proportions of the respective oils may each range between 1–99%, by volume, but may preferably fall within the range of substantially 30–70% respectively depending on the targeted microbe. Each or both of the two oils may be present in "increased" or "lessor" amounts, proportionally, depending on the targeted microbes.

According to another aspect of the present invention there is provided a method of preparing an antimicrobial composition, substantially as described above, for having effect against gram negative microbes by increasing the proportion of *melaleuca alternifolia* in the composition.

According to another aspect of the present invention there is provided a method of preparing an antimicrobial composition, substantially as described above, for having effect against gram positive microbes by increasing the proportion of *leptospermum scoparium* oil in the composition.

According to another aspect of the present invention there is provided a method of increasing the potency of the broad-spectrum antimicrobial composition, substantially as described above, comprising the step of extracting high potency fractions of the oils and incorporating them into the composition.

The high potency fractions may be used in whole or diluted form and in combination or singly.

According to further aspects of the present invention there is provided broad spectrum antimicrobial compositions, produced according to the above methods.

According to a further aspect of the present invention there is provided an antimicrobial composition substantially as described above, containing a fraction of *melaleuca alternifolia* oil having high potency, as defined hereinafter.

According to a further aspect of the present invention there is provided an antimicrobial composition substantially as described above comprising predominantly enhanced terpinen-4-ol.

According to a further aspect of the present invention there is provided an antimicrobial composition containing a fraction of *melaleuca alternifolia* oil having lower potency, as defined hereinafter.

According to a further aspect of the present invention there is provided an antimicrobial composition substantially as described above comprising predominantly compounds selected from one or more of the following group: pinenes, myrcene, 2-carene, limonene, gamma terpinen and lower levels of Terpinen-4-ol.

According to a further aspect of the present invention there is provided an antimicrobial composition, containing a fraction of *leptospermum scoparium* having high potency, as defined hereinafter.

According to a further aspect of the present invention there is provided an antimicrobial composition substantially as described above comprising predominantly enhanced levels of flavesone, isoleptospermone and leptospermone.

According to another aspect of the present invention there is provided an antimicrobial composition containing a fraction of *leptospermum scoparium* having lower potency, as defined hereinafter.

According to a further aspect of the present invention there is provided an antimicrobial composition substantially as described above comprising predominantly lower levels of monoterpines and/or lower concentrations of flavesone, isoleptospermone and leptospermone.

Combinations and dilutions of the above whole oils, fractions or dilutions thereof and/or combinations thereof are also within the scope of the present invention given the hitherto unknown finding that the said combinations provide a novel and effective broad spectrum antimicrobial composition.

Applications of same including those relating to antimicrobial treatments in general together with those relating to the treatment or prevention of minor microbial related ailments or conditions in humans are also within the scope of the present invention.

EXAMPLES

Further aspects of the present invention will become apparent from the following description that is given by way of example only and with reference to the accompanying tables:

TABLE 1

Greatest Dilution Showing Microcidal Effect

| Organism | *Melaleuca alternifolia* | *Leptospermum scoparium* |
| --- | --- | --- |
| *Klebsiella pneumoniae* | 1:800 | <1:10 |
| *E. coli* | 1:500 | <1:10 |
| *Staphylococcus aureus* | 1:400 | 1:1500 |
| *Streptococcus faecalis* | 1:400 | 1:2000 |
| *Streptococcus pyogenes* | 1:5000 | 1:2000 |
| *Pseudomonas aeruginosa* | <1:10 | <1:10 |
| *Candida albicans* | 1:700 | <1:30 |
| *Tricophyton mentagrophytes* | 1:1000 | 1:1000 |
| *Aspergillus niger* | <1:50 | <1:50 |
| *Propionibacterium acnes* | 1:900 | 1:700 |
| *Listheria Monocytogenes* | 1:700 | 1:2000 |
| *Proteus vulgaris* | 1:500 | <1:10 |

TABLE 2

Greatest Dilution Showing Microcidal Effect

| Organism | *Melaleuca Alternifolia* | *Leptospermum Scoparium* |
| --- | --- | --- |
| Gram positive *Staphylococcus aureus* | 1:400 | 1:1500 |
| Gram positive *Streptococcus pyogenes* | 1:1500 | 1:2000 |
| Gram negative *E. coli* | 1:500 | <1:10 |
| Gram negative *Ps. aeruginosa* | 1:40 | <1:10 |

TABLE 3

Greatest Dilution Showing Microcidal Effect for a Mixture of Equal Parts of *Melaleuca alternifolia* and *Leptospermum scoparium* Oils

| *E. coli* | 1:100 |
| --- | --- |
| *Staphylococcus aureus* | 1:1000 |

TABLE 4

Greatest Dilution Showing Microcidal Effect for High Potency *Melaleuca alternifolia* Fraction

| *E. coli* | 1:600 |
| --- | --- |
| *Staphylococcus aureus* | 1:900 |

TABLE 5

Greatest Dilution Showing Microcidal Effect for High Potency *Leptospermum scoparium* Fraction

| *E. coli* | <1:10 |
| --- | --- |
| *Staphylococcus aureus* | >1:2000 |

TABLE 6

Greatest Dilution Showing Microcidal Effect for Low Potency *Melaleuca alternifolia* Fraction

| *E. coli* | <1:10 |
| --- | --- |
| *Staphylococcus aureus* | 1:1000 |

TABLE 7

Greatest Dilution Showing Microcidal Effect for Low Potency *Leptospermum scoparium* Fraction "7"

| *E. coli* | 1:600 |
| --- | --- |
| *Staphylococcus aureus* | 1:400 |

TABLE 8

Greatest Dilution Showing Microcidal Effect for Varying Concentrations of High Potency *Melaleuca alternifolia* and *Leptospermum scoparium* Fractions

| Composition (by Volume) | *E. coli* | *Staphylococcus aureus* |
| --- | --- | --- |
| 45% *Melaleuca alternifolia* + 55% *Leptospermum scoparium* fraction | 1:100 | >1:2000 |
| 50% *Melaleuca alternifolia* + 50% *Leptospermum scoparium* fraction | 1:200 | >1:2000 |
| 55% *Melaleuca alternifolia* + 45% *Leptospermum scoparium* fraction | 1:200 | >1:2000 |
| 60% *Melaleuca alternifolia* + 40% *Leptospermum scoparium* fraction | 1:250 | 1:2000 |
| 65% *Melaleuca alternifolia* + 35% *Leptospermum scoparium* fraction | 1:300 | 1:1750 |

TABLE 9

Greatest Dilution Showing Microcidal Effects for 90% Fraction "Y" *Melaleuca alternifolia* and 10% *Leptospermum scoparium* Fraction "8" compared to 100% *Melaleuca alternifolia* and 100% *Leptospermum scoparium* oils

| Organisms | *Melaleuca alternifolia* | *Leptospermum scoparium* | Fractions 90% Melaleuca "Y" 10% Leptospermum "8" |
| --- | --- | --- | --- |
| *Escherichia coli* | 1:500 | <1:10 | 1:900 |
| *Pseudomonas aeruginoas* | <1:10 | <1:10 | 1:10 |

TABLE 9-continued

Greatest Dilution Showing Microcidal Effects for 90% Fraction "Y"
Melaleuca alternifolia and 10% Leptospermum scoparium Fraction "8"
compared to 100% Melaleuca alternifolia and 100% Leptospermum
scoparium oils

| Organisms | Melaleuca alternifolia | Leptospermum scoparium | Fractions 90% Melaleuca "Y" 10% Leptospermum "8" |
|---|---|---|---|
| Proteus vulgaris | 1:500 | <1:10 | 1:700 |
| Klebsiella pneumoniae | 1:800 | <1:10 | 1:1000 |
| Staphyloccus aureus | 1:400 | 1:1500 | 1:900 |
| Streptococcus pyogenes | 1:1500 | 1:2000 | <1:2000 |
| Streptoccus faecalis | 1:400 | 1:2000 | 1:700 |
| Listheria Monocytogenes | 1:700 | 1:2000 | 1:750 |
| Propionibacterium acnes | 1:900 | 1:700 | 1:800 |
| Aspergillus niger | <1:50 | <1:50 | 1:300 |
| Tricophyton mentagrophytes | 1:1000 | 1:1000 | 1:1000 |

BEST MODES OF CARRYING OUT THE INVENTION

Both the essential oils prepared from *melaleuca alternifolia* and *leptospermum scoparium* kill, to a greater or lesser extent, a wide range of microorganisms as is shown in Table 1.

The applicant has found that *Melaleuca alternifolia* oil is relatively more potent at killing gram negative organisms eg *Eschericia coli,* than is *leptospermum scoparium* oil. *Leptospermum scoparium* oil however is found to be relatively more potent at killing gram positive organisms eg *Staphylococcus Aureus,* than is *melaleuca alternifolia* oil (see Table 2).

An aspect of the present invention is the production of an antimicrobial composition (in the form of an oil) with a unique and surprisingly broad spectrum and selective potency against a wide range of micro-organisms. This is achieved in one embodiment by mixing whole *melaleuca alternifolia* oil with whole *leptospermum scoparium* oil at varying concentrations (Table 3).

According to another embodiment of the present invention, particular fractions of the oils of both species may be extracted and combined according to the desired spectrum of the fractions and the potency required and/or the microbes to be targeted.

For example, it appears that the most potent components (that is "high potency") of *melaleuca alternifolia* oil against microorganisms, according to gas chromatography (GC), occur between approximately relative index (RI), 920 and 1142 (Table 4). These components can alternatively be characterised as fractions containing enhanced Terpinen-4-ol levels.

Further, the most potent components (that is "high potency") of *leptospermum scoparium* oil against microorganisms, according to GC, occur approximately between RI 1482 and 1610 (Table 5). These components can alternatively be characterised as or include fractions containing enhanced levels of Flavesone, Isoleptospermone and Leptospermone.

In the context of this specification, the term "enhanced" means an increased amount over the whole base oil.

RI components in the case of *melaleuca alternifolia* oil between approximately 1179 and 1610, namely fractions containing compounds selected from the group comprising pinene, myrcene, limonene, gamma terpinene and lower levels of terpinen-4-ol, retain "low potency" antimicrobial action and may still be useful on their own or in mixtures with other oil fractions (Table 6).

RI components in the case of *leptospermum scoparium* oil between approximately 920 and 1476, namely fractions containing compounds selected from the group comprising monoterpines and low concentrations of Flavesone, Isoleptospermone and Leptospermone retain "low potency" antimicrobial action and may still be useful on their own or in mixtures with other oil fractions (Table 7).

It will accordingly be appreciated that the low potency fractions of both species may be used where the antimicrobial effect of the preparation is required to be less potent, perhaps in cosmetic treatments, mild antibacterial face washes and the treatment of minor medical ailments, or for non-human applications. Alternatively the low potency fractions may be used to supplement other higher potency fractions.

To create a broad spectrum "high potency oil", the high potency fractions of *melaleuca alternifolia* oil are mixed with the high potency fractions of *leptospermum scoparium* oil (Table 8 and Table 9). The measuring and mixing may be achieved in any manner known in the art, and utilise any desired quantity ratios or concentration of the oil fractions.

The proportions of the mixtures as discussed above can be varied to change the degree of potency against any particular group of microbes. Again, no strict formula applies in terms of changing proportions as it will be apparent to the art skilled worker, and having regard to Table 8 and Table 9, what degree of variation may be required in relation to a desired end usage.

For example, as shown in Table 8 by decreasing the percentage of the high potency *melaleuca alternifolia* oil fraction (RI 920–1142), and increasing the percentage of high potency *leptospermum scoparium* oil fraction (RI 1482–1610), the resultant oil mixture is more potent against gram positive organisms eg *Staphylococcus Aureus*.

Similarly, by increasing the percentage of the high potency *melaleuca alternifolia* oil fraction (RI 920–1142) and decreasing the percentage of the high potency *leptospermum scoparium* oil fraction (RI 1482–1610) the resultant oil mixture is more potent against gram negative organisms eg *Escherecia Coli*. Quantities in this example varied by up to 15% from equal quantities but quantities between 1–99% of each oil respectively are within the scope of the present invention.

Fractions of the oils are produced by any known fractionation method, for example supercritical $CO_2$, molecular distillation, steam stripping and solvent fractionation. Depending on the proportion of fractions of both oils mixed together, the concentrations and characteristics of the original oils may be altered. Particularly, where 90% high potency fraction of *melaleuca alternifolia* oil with 10% high potency fraction of *leptospermum scoparium* oil (Table 9) is used, a broad spectrum, high potency (and reduced perfume) composition is produced.

It can be seen that the present invention relates to methods of combining *melaleuca alternifolia* oil and *leptospermum scoparium* oil, or any combination of said whole oils, dilutions or fractions, to produce compositions with varying spectrum, and activity against microorganisms. This is highly advantageous over prior art existing uses of whole oils individually.

Aspects of the present invention have been described by way of example only and it should be appreciated that modifications and additions may be made thereto without departing from the scope thereof as defined in the appended claims.

What is claimed is:

1. An antimicrobial composition comprising the oils of *Leptospermum scoparium* (*L. scoparium*) and *Melaleuca alternifolia* (*M. alternifolia*), and/or fractions thereof, wherein the oils and/or fractions thereof are in altering proportions so as to target specific organisms or microbes, and wherein the oils and/or fractions thereof comprise substantially 30–70%, by volume, of the composition.

2. The antimicrobial composition of claim 1, wherein the proportion of *M. alternifolia* oil is higher than that of *L. scoparium* oil to target gram negative organisms.

3. The antimicrobial composition of claim 2, comprising 55–90% high potency fraction of *M. alternifolia* oil and 10–45% high potency fraction of *L. scoparium* oil.

4. The antimicrobial composition of claim 2, comprising 55% high potency fraction of *M. alternifolia* oil and 45% high potency fraction of *L. scoparium* oil.

5. The antimicrobial composition of claim 2, comprising 60% high potency fraction of *M. alternifolia* oil and 40% high potency fraction of *L. scoparium* oil.

6. The antimicrobial composition of claim 2, comprising 65% high potency fraction of *M. alternifolia* oil and 35% high potency fraction of *L. scoparium* oil.

7. The antimicrobial composition of claim 2, comprising 90% high potency fraction of *M. alternifolia* oil and 10% high potency fraction of *L. scoparium* oil.

8. The antimicrobial composition of claim 1, wherein the proportion of *L. scoparium* oil is higher than that of *M. alternifolia* oil to target gram positive organisms.

9. The antimicrobial composition of claim 1, comprising a high potency fractions of *L. scoparium* and *M. alternifolia* oils.

10. The antimicrobial composition of claim 9, comprising high potency fractions of both *L. scoparium* and *M. alternifolia* oils.

11. The antimicrobial composition of claim 9, comprising the high potency fraction of *L. scoparium* oil.

12. The antimicrobial composition of claim 9, wherein the high potency fraction of *L. scoparium* oil has a relative index (RI) between 1482 and 1610.

13. The antimicrobial composition of claim 9, wherein the high potency fractions of *M. alternifolia* oil comprises compounds selected from the group consisting of Flavesone, Isoleptospermone and Leptospermone.

14. The antimicrobial composition of claim 9, comprising the high potency fraction of *M. alternifolia* oil.

15. The antimicrobial composition of claim 9, wherein the high potency fraction of *M. alternifolia* oil has an RI between 920 and 1142.

16. The antimicrobial composition of claim 9, wherein the high potency fractions of *M. alternifolia* oil contains Terpinen-4-ol.

17. The antimicrobial composition of claim 1, comprising a combination of low potency fractions of *L. scoparium* and *M. alternifolia* oils.

18. The antimicrobial composition of claim 17, wherein the low potency fraction of *L. scoparium* oil have an RI between 920 and 1746.

19. The antimicrobial composition of claim 17, wherein the low potency fraction of *L. scoparium* oil comprise compounds selected from the group consisting of monoterpins, and low concentrations of Flavesone, Isoleptospermone and Leptospermone.

20. The antimicrobial composition of claim 17, wherein the low potency fraction of *M. alternifolia* oil has an RI between 1179 and 1610.

21. The antimicrobial composition of claim 17, wherein the low potency fraction of *M. alternifolia* oil comprises compounds selected from the group consisting of pinene, myrcene, limonene, gamma terpinene and a low concentration of terpinen 4-ol.

22. The antimicrobial composition of claim 1, comprising a combination of high and low potency fractions of *L. scoparium* and *M. alternifolia* oils.

23. A method for the treatment of microbial infection comprising administration of a composition comprising an effective amount of a combination of oils of *Leptospermum scoparium* (*L. scoparium*) and *Melaleuca alternifolia* (*M. alternifolia*).

* * * * *